(12) United States Patent
Osborn

(10) Patent No.: US 7,538,758 B2
(45) Date of Patent: *May 26, 2009

(54) ABSOLUTE COORDINATE, SINGLE USER-INTERFACE ELEMENT POINTING DEVICE

(75) Inventor: John J. Osborn, San Anselmo, CA (US)

(73) Assignee: Westing Software, Inc., San Anselmo, CA (US)

( * ) Notice: Subject to any disclaimer, the term of this patent is extended or adjusted under 35 U.S.C. 154(b) by 674 days.

This patent is subject to a terminal disclaimer.

(21) Appl. No.: 11/174,131

(22) Filed: Jun. 30, 2005

(65) Prior Publication Data

US 2005/0243074 A1    Nov. 3, 2005

Related U.S. Application Data

(63) Continuation-in-part of application No. 10/617,596, filed on Jul. 11, 2003, now Pat. No. 7,126,582.

(60) Provisional application No. 60/452,835, filed on Mar. 7, 2003.

(51) Int. Cl.
*G09G 5/08* (2006.01)
(52) U.S. Cl. .............................. 345/157; 341/20; 74/471
(58) Field of Classification Search ................ 345/156, 345/157, 160, 161, 163, 184; 74/471; 463/37, 463/38; 341/20
See application file for complete search history.

(56) References Cited

U.S. PATENT DOCUMENTS

| | | | | | |
|---|---|---|---|---|---|
| 4,444,997 | A | * | 4/1984 | Danish et al. | 178/18.01 |
| 5,821,921 | A | * | 10/1998 | Osborn et al. | 345/157 |
| 6,061,004 | A | * | 5/2000 | Rosenberg | 341/20 |
| 6,084,571 | A | * | 7/2000 | De Gotari | 345/157 |
| 6,107,991 | A | * | 8/2000 | Osborn | 345/157 |
| 6,215,478 | B1 | * | 4/2001 | Yeh et al. | 345/173 |
| 6,806,959 | B2 | * | 10/2004 | Tukker | 356/484 |
| 6,831,629 | B2 | * | 12/2004 | Nishino et al. | 345/157 |
| 2004/0155862 | A1 | * | 8/2004 | Higginson | 345/156 |

* cited by examiner

Primary Examiner—Richard Hjerpe
Assistant Examiner—Tom V Sheng
(74) Attorney, Agent, or Firm—Michael A. Kaufman, Esq.

(57) ABSTRACT

A pointing device includes a single control element to provide a user with absolute coordinate information and to enable user control of a computer cursor and emulation of mouse clicks. User movement of the single control element in an (x-y) plane preferably moves an optically reflective surface relative to an optical sensor system stationary within the device housing, such movement precluding rotation relative to the (x-y) plane. Mouse clicking may be emulated by moving the single control element up or down and/or by tilting relative to the (x-y) plane. Alternatively mouse clicking may be emulated by user activation of left and right sensor type switches or sensors. The device may be used by handicapped persons who can control cursor movement and mouse clicking using the single control element.

19 Claims, 10 Drawing Sheets

ABSOLUTE COORDINATE, SINGLE USER-INTERFACE ELEMENT POINTING DEVICE

PRIORITY TO CO-PENDING APPLICATIONS

This is a continuation-in-part application from applicant's co-pending U.S. patent application Ser. No. 10/617,596 was filed Jul. 11, 2003 entitled "Absolute Coordinate, Single User-interface Element Pointing Device", which application claimed priority from applicant's U.S. provisional patent application Ser. No. 60/452,835 filed on 7 Mar. 2003, entitled "Absolute Coordinate, Single User-interface Element Pointing Device".

FIELD OF THE INVENTION

The invention relates generally to mouse-like pointing devices, and more particularly to pointing devices that reduce stress and repetition of user movements, and provide the user with absolute coordinate information and a single interface element useable to move a cursor, to left click, and to right click, and to fabricating such devices with a form factor small enough to fit within a standard computer keyboard, if desired.

BACKGROUND OF THE INVENTION

Pointing devices for use with computers and other companion electronic equipment are known in the art and include trackballs, joysticks, and variations of the computer "mouse". Typically such devices require that the user move one element to control a cursor on a computer display, and then press or activate separate buttons to accomplish so-called "left-clicks" and "right-clicks". Further it is common that the user must hold such devices in a fairly rigid position during use. While such tasks may not be overly challenging for many users, these tasks can be overwhelming to handicapped users, as will now be described.

A mouse or a trackball typically has a rotatable spherical element that the user moves over a fixed surface such as a desktop to cause movement of a cursor on a computer display. However such pointing devices are not absolute coordinate devices in the sense that the user cannot tell by looking at the device where on the computer display the cursor may be found. Conventional pointing devices include one or more user-activated buttons, for example one button to left-click (and left double-click) and perhaps a second button to right-click. These different click functions can cause different menu options to appear on the computer screen, or can command a program to execute (in the case of a left double-click). A generic mouse weighs perhaps 4 oz. and is perhaps 2" wide, 5" long, and 1" in height. Commonly "left-click" and "right-click" buttons are located on the upper mouse surface, and are pressed, respectively, with the first and second fingers of the user's hand. Using the mouse to move a computer cursor on a display requires that the user move the entire mass of the mouse on the fixed surface such that the spherical element in the bottom of the mouse rotates.

More recently, the so-called optical mouse has found acceptance as a computer input device. An optical mouse often has the form factor of the older rotatable ball device. However instead of user-movement resulting in detectable rotation of a ball, an optical mouse replaces a rotatable ball with an optical emitter that directs light onto the work surface, and an optical sensor that detects light reflected by the work surface. As the user manipulates the mouse across the work surface, the optical sensor can discern relative changes in position by detecting the variation in different regions of the work surface, which variations typically are not apparent to the unaided eye. Exemplary optical mice are described in U.S. Pat. No. 6,281,882 (2001) and U.S. Pat. No. 6,433,780 (2002) to Gordon. However, manipulating an optical mouse requires essentially the same manual dexterity as manipulating a more conventional mouse, which dexterity is often not available to all would be users.

Prior art pointing mechanisms such as digitizer tablets can provide a degree of absolute coordinate information, but only while the digitizer stylus is in contact with the tablet surface. For instance if the stylus is contacting the upper right corner of the tablet, the user knows that the cursor will be in the upper right corner of the associated computer display. However as soon as the stylus is lifted from the digitizer tablet, the user can no longer look at the tablet and discern where on the computer display the cursor will be found. The stylus functions as the user-interface element to manipulate the cursor, and typically can be used to emulate left mouse-clicking.

But many users, especially physically handicapped users, find it difficult if not impossible to use prior art pointing mechanisms. Grasping and moving mice, or grasping and moving trackball devices to manipulate a cursor and then having to move a finger to click buttons may literally be impossible if the user suffers from carpal tunnel syndrome, arthritis, or perhaps has a hand prosthesis. Further, the inability to change how the user interacts with such devices promotes repetitive stress syndrome. For example, left mouse clicking will almost always require clicking a button on the left portion of the device. It is this sheer repetitiveness of user-interaction, coupled with the amount of user-generated force associated with using a conventional mouse or trackball device day-in and day-out that contributes to repetitive stress injury (RSI), even to an otherwise healthy user. A single user-interface element would be preferable, where the single element could be used to achieve cursor movement, and carry out the various mouse click functions. Also useful would be the ability to somewhat modify how the equivalent of mouse-clicking is carried out with a device. Even for non-handicapped users, the requirement of maintaining one hand on the device while pressing button(s) with a finger in a repetitive position, day-in, day-out, can result in physical disability, including tendonitis and carpal tunnel syndrome.

Some prior art pointing devices such as pressure or touch-pads found on modern laptops, or the so-called TrakPointer™ mechanism found on IBM™ laptops can provide a dual function user-interface element that can be used for cursor movement and for left-clicking. However such devices do not provide absolute coordinate information to the user, do not provide right-clicking, and can be difficult to maneuver, especially for the handicapped.

U.S. Pat. No. 5,821,921 (1998) and U.S. Pat. No. 6,107,991 (2000) to Osborn (applicant herein), which patents are incorporated herein by reference, disclosed pointing devices that provided the user with absolute coordinate information. The pointer mechanisms disclosed in these two patents included a user-gripable handle-like element that could better enable users, including handicapped users, to control cursor movement on a computer screen. The device described in Osborn '921 includes a peg-like element that a user could grasp to manipulate a cursor, and that could be pushed downward to emulate left mouse-clicking. The undersurface of the element would be moved by the user over a glide surface, and various resistive and/or optical mechanisms would determine the amount of movement in orthogonal x and y axes. Alternate embodiments of the '921 device included additional switches that a non-handicapped user could readily manipulate to emulate left and right mouse clicks. Among the advantages provided by devices according to the Osborn '921 and '991 patents was the substantial decrease in the magnitude of the mass of what the user was required to manipulate. Understandably for many handicapped users, and indeed for non-handicapped users, it is advantageous if computer control can be achieved while manipulating a smaller mass.

While the Osborn '921 and '991 pointing devices were absolute coordinate devices, there still was room for improvement. It turned out that double-clicking with the devices was difficult, especially for the handicapped. Excessive mechanical movement between the user-mechanism and the glide surface could occur between the movement of the first click and the second click. If the movement exceeds about three pixels on the computer display, the computer software will recognize two discrete and somewhat spaced-apart left mouse clicks, rather than a single left mouse double-click. In essence, while friction between the interface element and the underlying glide surface should be low for ease of user-controlled cursor movement, too low a coefficient of friction makes double-clicking difficult due to interface element movement between the two clicks.

What is needed is a pointing device with a single user-interface element that can be manipulated to move a cursor on a computer screen, while providing the ability to maintain absolute coordinate information. Preferably the single element should be user-manipulable to emulate single and double left mouse-clicks and also a right mouse click, and should be manipulable even by handicapped users. Preferably the mass of the user-manipulated single-element should be low to reduce magnitude of user-force required to manipulate the device, thus decreasing user fatigue and reducing likelihood of RSI. Preferably the device should allow the user to alter how mouse-clicking is carried out, to reduce repetitiveness associated with using the device, thus further reducing likelihood of RSI. Preferably the device should include a glide surface having a dynamic coefficient of friction that provides smooth rapid glide movement representing cursor movement, but that exhibits a higher coefficient of friction during mouse clicks to minimize undesired movement between mouse clicks. Further, such a device should be implementable in a form factor allowing device fabrication within a computer keyboard or laptop computer or other computer appliance, if desired. Regardless of the device is implemented, device output to the companion computer or other equipment should of course be in an industry standard output format.

The present invention provides such a pointing device.

SUMMARY OF THE INVENTION

Embodiments of the present invention provide an absolute coordinate pointer device having a single control element with which even a handicapped user can manipulate a cursor on the display of a companion computer (or other electronic system). Although the device can provide absolute coordinate information; in some applications the user may wish to adjust cursor velocity and/or acceleration using software to maximize cursor pointing accuracy. Preferably by manipulating the single control element in the (x-y) plane a light weight piece of optically reflective material is moved by the user. The invention includes a mechanism that constrains movement of the optically reflective materially to movement parallel to the (x-y) axes, without permitting rotational movement. The invention includes a preferably optical sensor system that is fixedly mounted within the device housing. The sensor system senses control element movement by examining light reflected as the optically reflective material is moved responsive to user movement of the control element. The sensor system outputs cursor movement information. As a result, there is little user fatigue because the mass of what the user manipulates to control cursor movement is essentially very small, namely the mass of the control element, the mass of a small platform, and the mass of the optically reflective material. This is in contrast to prior art devices in which the entire device must be manipulated by the user.

The single control element can be user-changeable such that a pen-shaped element can be used for users who can grip such an element, a prosthesis-engageable element can be used for users who use prosthesis, and so forth.

In some embodiments, mouse clicking is emulated by moving the single control element vertically up or down, e.g., in a direction normal to the (x-y) plane. In other embodiments, mouse clicking is emulated by tilting the single control element in a direction not normal to the (x-y) plane, e.g., tilting left or right. In yet other embodiments, mouse click is emulated by the user pressing to the left or right of the single control element so as to slightly tilt a small platform extending left and right of the single control element. In other embodiments, the user can emulate mouse clicks by directly pressing a sensor switch to the left or right of the single control element.

In some embodiments, the single control element is moved over a film-like glide surface whose top layer preferably exhibits a dynamic coefficient of friction such that more friction is present during slow movement such as during a double-click than during rapid movement. The top layer of the glide surface preferably includes a sheet of polycarbonate vellum material, or material such as medical X-ray film. Such glide surface material tends to reduce unintended cursor movement during double-clicking operations.

In some embodiments, the mechanism to constrain movement of the optically reflective material includes at least one longitudinal groove and vane disposed parallel to the x-axis and at least one longitudinal groove and vane disposed parallel to the y-axis. Either the vanes or the grooves are formed in a small platform that is moved by the single control element, and the other of the fins or grooves are formed in a portion of the device housing. A sliding interlocking cooperation between the vanes and grooves precludes rotation of the small platform as the single control element is manipulated, and precludes rotational movement of the optically reflective material. In other embodiments, the mechanism to constrain movement of the optically reflective material is a pantographic mechanism. The pantograph mechanism includes a first member that is moved by user-manipulation of the single control element, and includes a second member that moves the optically reflective material parallel to the x-axis and y-axis, thus precluding rotational movement. Various embodiments of the invention can be fabricated with a form factor sufficiently small to fit within the confines of a conventional keyboard, laptop computer, or other computer device, if desired.

Regardless of the implementation of the device, cursor movement data and emulated mouse-click data can be communicated to the companion computer (or other system) in conventional formats and media including, without limitation, a wired serial port, a wired parallel port, a wired USB port, a wireless coupling, including IR and/or RF energy. Likelihood of a user suffering repetitive stress injury (RSI) is reduced by reducing magnitude of stress by substantially reducing magnitude of the mass the user must move to move a cursor. Likelihood of the user suffering RSI is also reduced by reducing the repetitiveness associated with using the device, by allowing the user to readily alter the shape of the control element, and by altering the manner in which mouse clicking is commanded.

Other features and advantages of the invention will appear from the following description in which the preferred embodiments have been set forth in detail, in conjunction with their accompanying drawings.

DETAILED DESCRIPTION OF THE PREFERRED EMBODIMENT

Figure 1:
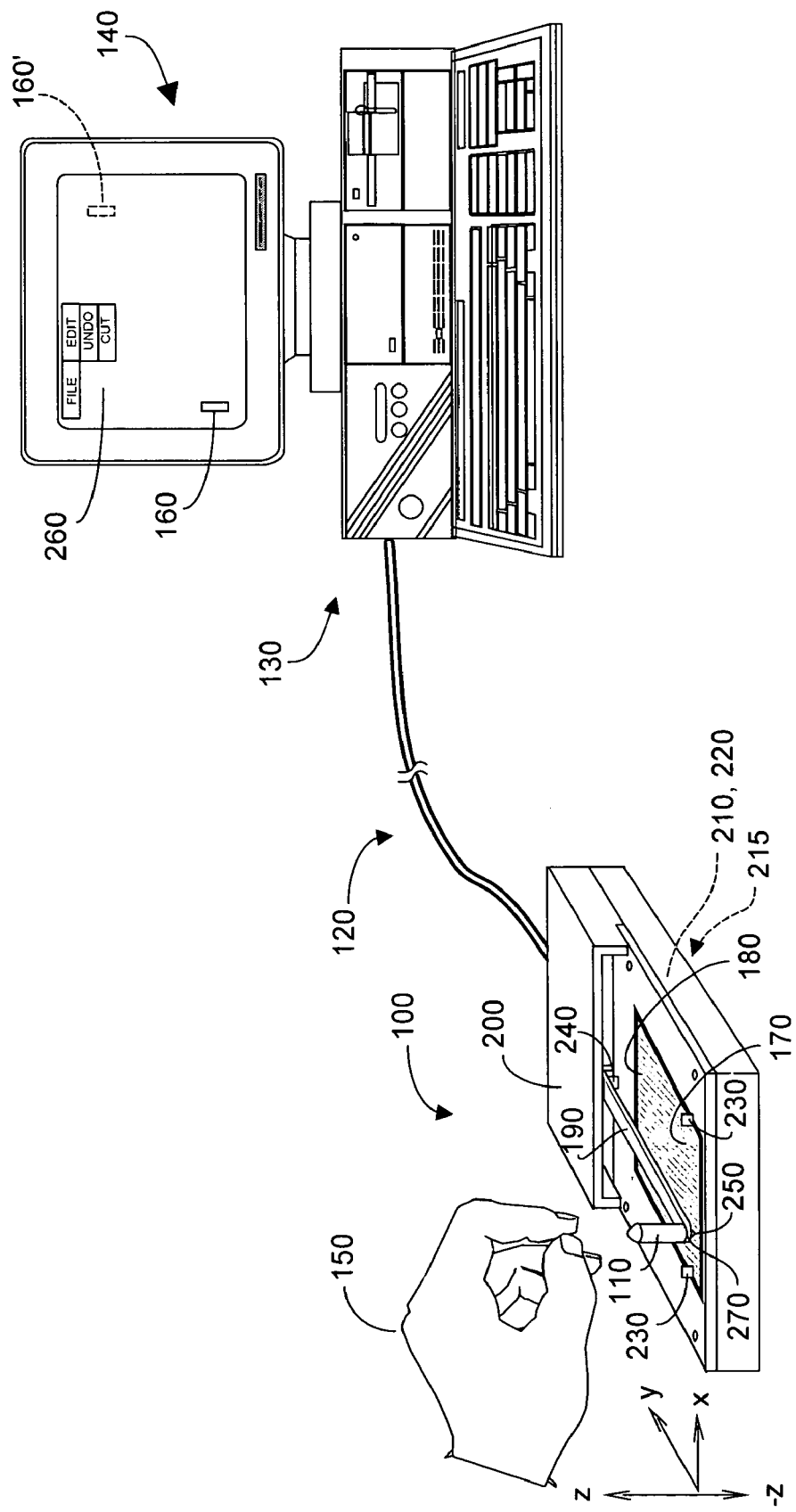
FIG. 1 depicts a first embodiment of the present invention.
Figure 6A:
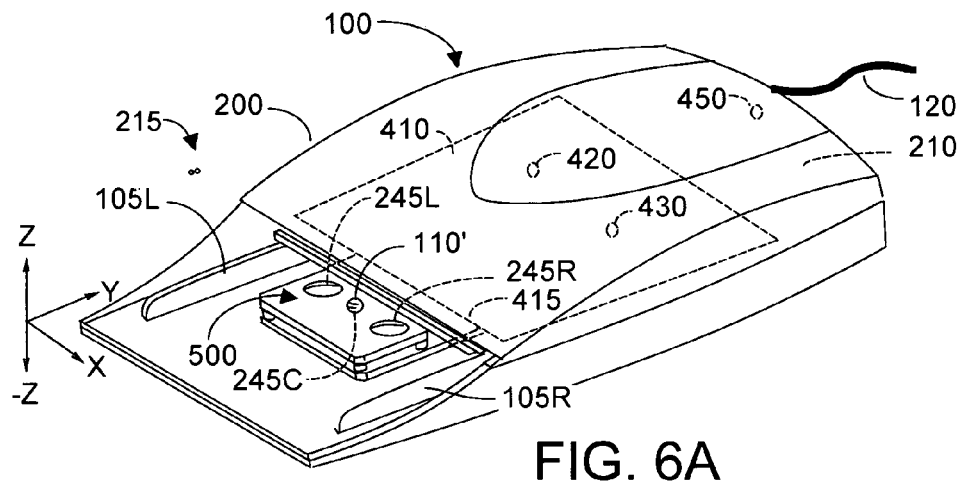
FIGS. 6A-6C are perspective views of a fourth embodiment of the present invention.

The description of the present invention commences with FIG. 6A. However it will be useful to first review the embodiments of applicant's parent application. FIG. 1 depicts an absolute coordinate pointer device 100 having a single control element 110 coupled via an interface 120 to a computer system 130 that includes a monitor or display 140. While interface 120 is depicted generically as a cable, it is to be understood that output signals from device 100 may instead be coupled to computer system 130 using infrared, radio signals, acoustic signals, among other communications media. Regardless of how the interface is implemented, output signals from device 100 will be received as input by computer system 130 in a format compatible with signals output from a generic off-the-shelf trackball and/or mouse input. It is further understood that while computer system 130 is shown as a PC-type computer, system 130 may in fact be a kiosk or other system to be controlled at least in part by an input device such as device 100.

As a user 150 grasps or otherwise manipulates control element 110, a cursor 160 is caused to move accordingly on display 140 as control element 110 moves across surface 170. (The user's hand 150 is shown spaced apart from control element 110 in FIG. 1 for ease of illustration.) Device 100 is termed an absolute coordinate pointer device in that a user can look at device 100 and know by the relative position between control element 110 and surface 170 where on display 140 the computer displayed cursor 160 will appear. In FIG. 1, for example, control element 110 is above the left lower corner region of surface 170, and accordingly cursor 160 is displayed at the left corner region of display 140. If user 150 manipulated control element 110 to another position on surface 170, cursor 160 would move accordingly on display 140. Thus if the control element 110 were moved to say the right corner region 180 of surface 170, display 140 would show the cursor in the right hand region, depicted as phantom cursor 160. This ability of device 100 to provide the user with absolute coordinate information is not present in conventional prior art pointing devices such as a mouse, a trackball, a joystick, or a trackpad.

While the present invention can provide absolute coordinate information, in some applications the user might elect to sacrifice absolute coordinate information to achieve more precise control over cursor movement. Most users of commercial software are aware that the operating system, perhaps Windows XP, or mouse software can be used to alter speed and acceleration movements of a mouse or trackball manipulated cursor on a computer screen. For example, suitable adjustment in Windows XP might involve the user going to Control Panel, selecting Mouse, and then adjusting Pointer Options to achieve a desired pointer (or cursor) speed characteristic. Thus, when device 100 is used in an absolute coordinate mode, moving control element 110 in FIG. 1 from the left-lower corner of surface 170 to the right-upper corner of surface 170 will move the cursor from position 160 to 160' on display 140. In this mode, the user can glance at device 100 and know from the position of control element 110 approximately where on display 140 the cursor will appear. However if mouse movement is adjusted using software, as described above, a smaller movement of control element 119 on surface 170 can result in a larger (or smaller) movement on display 140. In this mode, the absolute coordinate capability of device 100 is intentionally traded away by the user to achieve a desired different movement of the cursor.

Control element 110 is shown as a stub-like element in FIG. 1 that is attached to a cantilever arm 190 that projects out from the housing 200 of device 100. While arm 190 is shown as a single span, it could of course be triangular with the apex beneath control element 110, or U-shaped with the joining portion of the "U" beneath control element 110, among other configurations. The precise configuration will take into account the nature of the material comprising arm 190, e.g., plastic in the preferred embodiment, the length of the arm, the thickness of the material, and the projection length of the arm, typically about 1" or 2.5 cm. Surface 170 is sized to provide a convenient work area for the user, and is perhaps 2"×2" (2.54 cm×2.54 cm), although other dimensions could of course be used.

The present invention includes various embodiments of a mechanism 215 that constrains movement of control element 110 to movement along the x-axis and/or the y-axis, but precludes rotational movement. Mechanism 215 helps translate such x-axis, y-axis control element movements into non-rotational movements that will be sensed to move cursor 160 on a computer display 140. In some embodiments mechanism 215 includes interlocking grooves and fins, parallel to the x-axis and y-axis of device 100. Other embodiments implement mechanism 215 with a pantographic mechanism.

Referring to FIG. 1, in some embodiments, housing 200 contains mechanism 210 that translates at least planar movement of control element 110 along the x and y axes of surface 170 resistively (as disclosed in U.S. Pat. No. 5,821,921) or more preferably optically (as disclosed in U.S. Pat. No. 6,107, 991), which patents are incorporated herein by reference. Preferably, mechanism 215 includes a pantographic mechanism 220 that is coupled with an optical mechanism 210, such as disclosed in the '991 patent. Pantographic mechanism 220 is described later herein with respect to FIGS. 4A-4C, FIGS. 5A-5C, and FIG. 6.

In the '991 patent and the '921 patent, the planar surface upon which the equivalent of a control element was moved was typically made of a relatively frictionless material such as Teflon™ brand material. But often such surface was too smooth and made it difficult for a user to hold the control element in place relatively to the surface sufficiently long to complete two mouse clicks. In practice if relative movement between the control element and the surface exceeds a few display pixels, the operating system with the associated computer system will not recognize a double-click.

In some embodiments of the present invention, surface 170 preferably exhibits a dynamic coefficient of friction. By "dynamic coefficient of friction" it is meant that surface 170 has a relatively low effective coefficient of fraction as control element 110 is user-moved relatively rapidly across the surface, but exhibits a larger effective coefficient of friction as the velocity of the movement decreases. This characteristic of surface 170 enables a user to readily move control element 110 on the surface 170, while advantageously tends to hold control element in place as user movement slows or halts, for example in preparation for a double mouse click action. Experiments by applicant have disclosed that Accufilm™ matte finish vellum material such as manufactured by California corporation Bishop Graphics, Inc. works well. The material is a stable vinyl plastic sheet film such as business cards are often printed upon. Less preferably, yellow polycarbonate sheet material such as sold by Ain Plastics located in Mt. Vernon, N.Y., and even exposed or unexposed medical X-ray film exhibits the desired dynamic coefficient of friction characteristics. By way of comparison, undesired relative movement between the control element and underlying surface plane in devices disclosed in the '991 and the '921 patents could be as high as about ten pixels. By contrast, in one embodiment of the present invention where surface 170 is polycarbonate sheet material or X-ray film material, the undesired relative movement is on the order of perhaps three pixels, which is within the acceptable range of movement for double-click recognition for Windows 98, Windows 2000, Windows XP, among other operating systems.

Thus in an embodiment of the present invention, users, and especially handicapped users, are less plagued by problems associated with accelerated cursor movement followed by a halt and a desired double-click action. Using the described material for surface 170 allows even handicapped users to use device 100 to draw and otherwise manipulate cursor movement on an associated computer system, and to enable double-clicking action.

Typical computer type applications will call upon device 100 to enable a so-called left mouse click, a so-called right mouse click, and as noted above, a double mouse click. In FIG. 1, a spaced-apart optical transmitter-receiver 230, and/or micro-switches 240, 250 can be used to detect when control element 110 is lifted up (in the positive z-axis) or is pushed down (in the negative z-axis).

A downward push of control element 110 by user 150 in the negative z-axis deeper into surface 170 is sensed by mechanism 250 (or 230) and emulates a left mouse click. Similarly, two relatively rapid such movements are sensed by mechanism 250 (or 230) and emulate a double mouse click. When user 150 lifts control element 110 upward in the positive z-axis, away from surface 170, the movement is sensed by mechanism 240 (or other mechanism), and device 100 emulates a right mouse click.

It will be appreciated that user 150 need only manipulate the single control element 110 to draw pictures or otherwise move or control cursor 160 upon display 140, as well as to emulate left, right, and double mouse clicking. For handicapped users, the ability to control all of these functions with a single control element is highly advantageous, especially if the user does not have full use of his or her fingers. Thus even a handicapped user can select menu-type options 260 on display 140 using the single control element 110, according to embodiments of the present invention.

Different users may benefit from differently shaped control elements 170. Thus an attachment mechanism 270 preferably is used at the interface of control element 110 and arm 190 to facilitate changing the control element. If no change were desired, then mechanism 270 could be a permanent glue, or perhaps a threaded stud in control element 110 and mating threads in an opening defined in the underlying portion of arm 190. More preferably, mechanism could include a pair of strong magnets, where there is a bowl-like recess defined in the distal portion of arm 190 and a smooth mating rounded region at the lower distal end of control element 110. A strong magnet embedded in each, or perhaps a strong magnet in one and a piece of metal in the other would enable a flexible connection between element 110 and arm 190.

Figure 2:
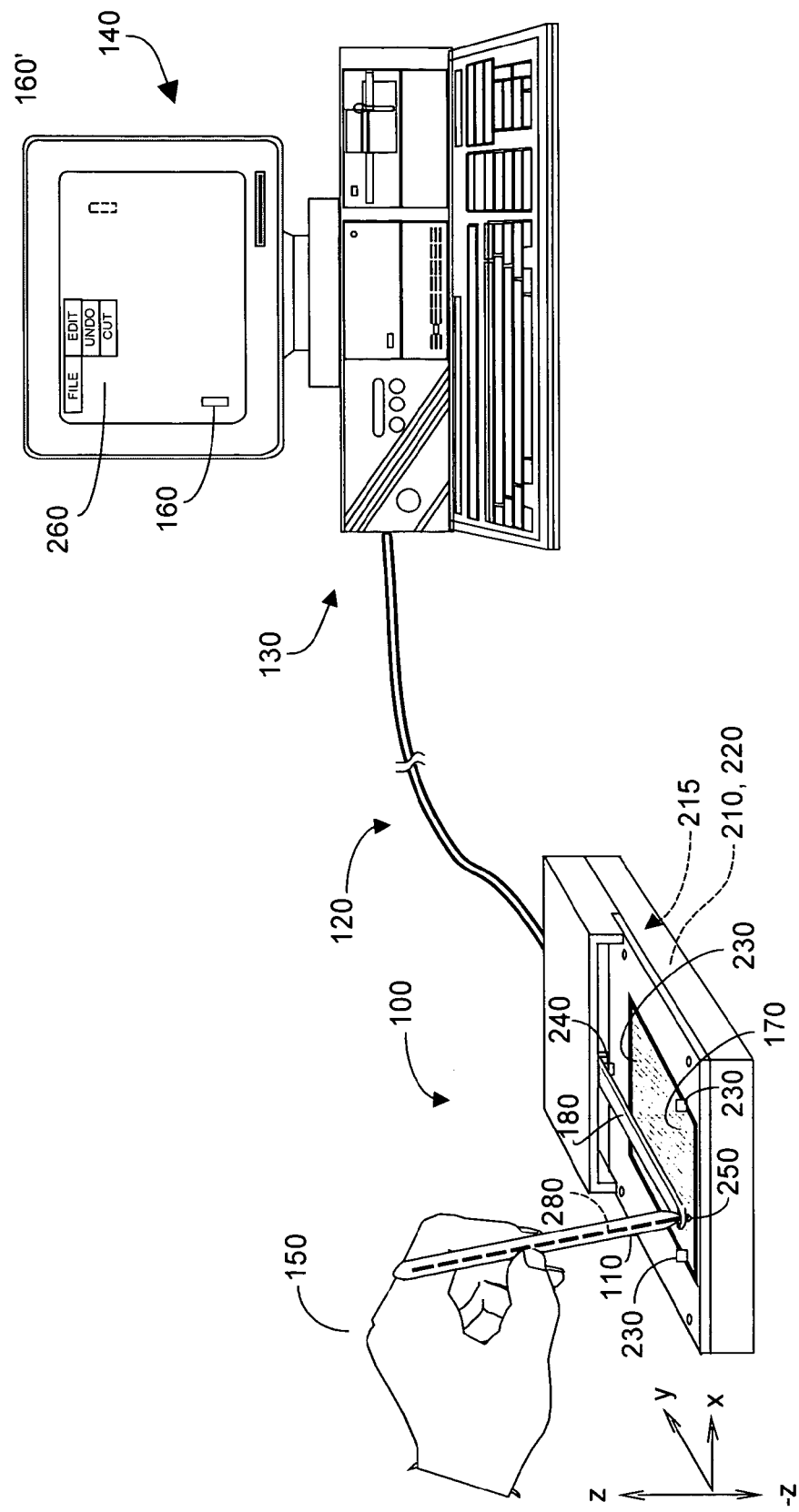
FIG. 2 depicts a second embodiment of the present invention.

FIG. 2 depicts such a flexible connection for device 100, where a longer, writing pen-like control element is now provided for a user 150 who prefers such a control element. In lieu of magnet pairs 270, a piece of elastic material 280 such as an elastic cord, could be disposed within a hollow control element 170. Cord 280 would be anchored at one end to an upper portion of the control element, and anchored at the lower end to the distal region of arm 180. Such a configuration would allow control element 110 to be moved into a position parallel to surface 170, for example when packaging device 110 for resale or shipment. Note that control element 170 could be the hollow shell of a used inexpensive ballpoint pen, with an elastic cord within. The use of such inexpensive components and construction would allow much of device 100 to be fabricated by unskilled users, perhaps even handicapped users in cottage industry type fabrication process.

Figure 3:
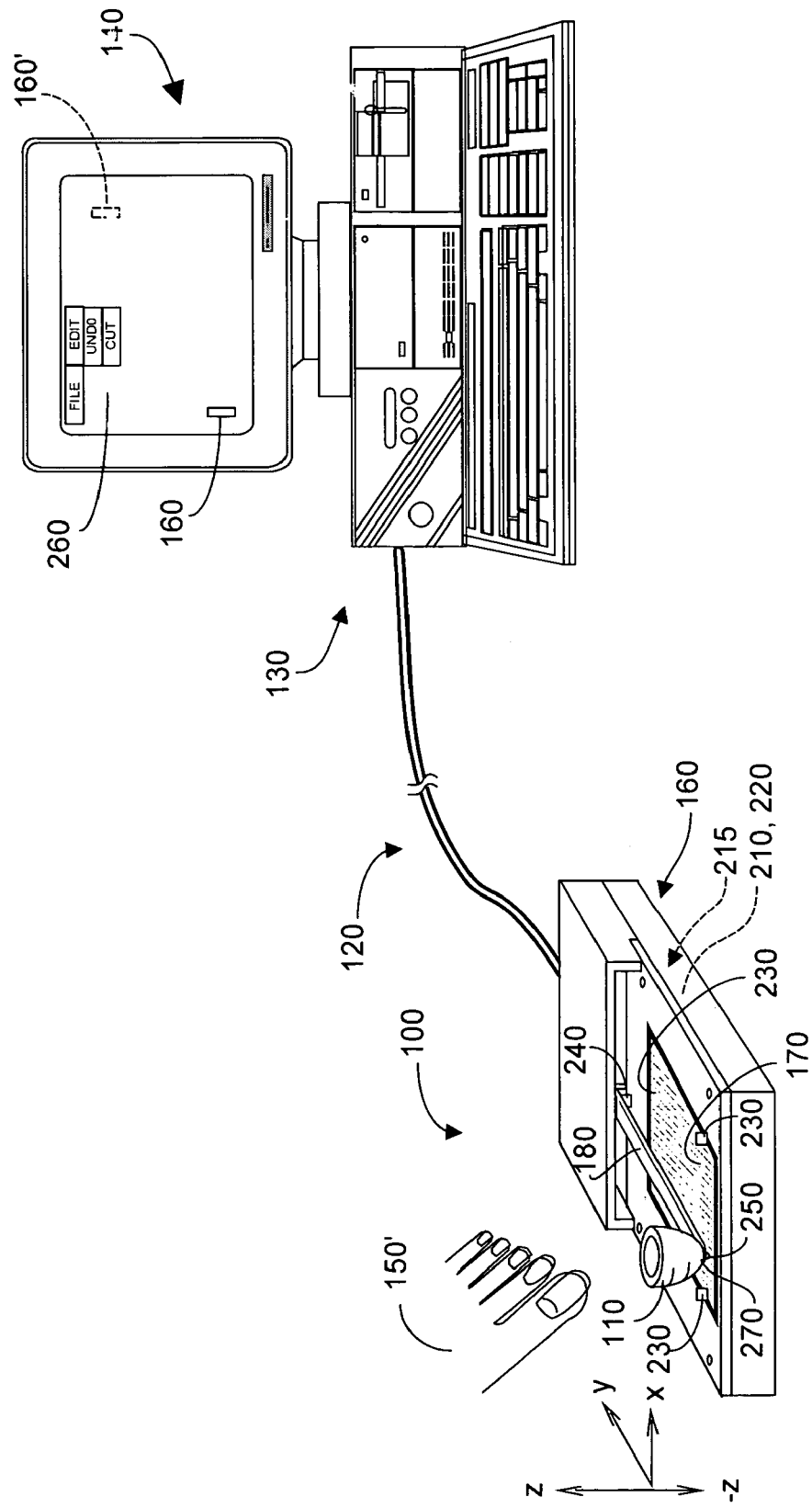
FIG. 3 depicts a third embodiment of the present invention.

Device 100 is not restricted to individuals who enjoy the use of one or more hands. FIG. 3 shows device 100 equipped with a toe-shaped cup control element 110, which a user 150' can engage with a toe. User 150 can thus control cursor 160 on display 140, and may even be able to implement proper left, right, and double mouse clicks, depending upon user agility with toe movement.

Figure 4A:
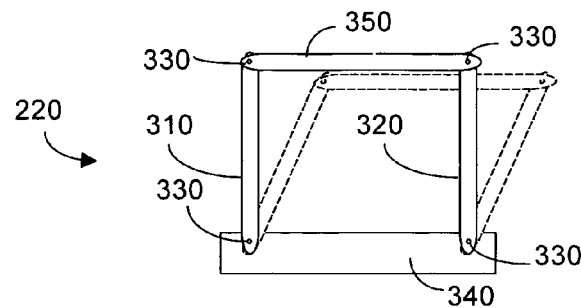
FIGS. 4A-4C are plan views of exemplary components used to provide a pantographically implemented embodiment of the present invention.
Figure 4B:
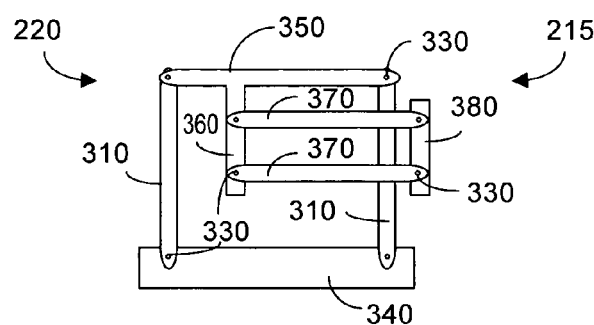
Figure 4C:
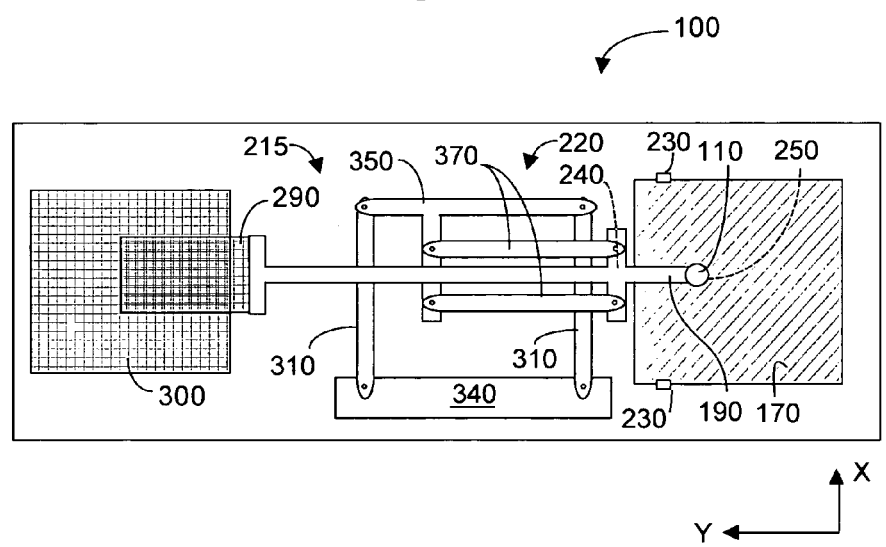

The plan views shown FIGS. 4A-4C depict embodiments in which constraint mechanism 215 comprises pantographic mechanism 200. Referring to FIG. 4C, mechanism 220 permits user manipulation of control element 110 at the distal end of arm 190 so as to move a film 290 relative to a stationary film 300, where each film has a grid-like pattern of parallel orthogonal lines of a desired pitch or granularity. Relative movement of film 290 will be in steps that are parallel to the x-axis and/or y-axis, with relative rotational movement being precluded. The use of such optical films was described in the '991 patent. Prior art electronics is used to sense and process light traveling through films 290 and 300, enabling enable device 100 to output mouse or trackball or trackpad type signals, recognizable by a companion computer system 130 (or other system).

In the '991 and '921 patents it was desired to constrain two components (one of which was user-manipulatable) such that movement in any direction was permitted, but rotation between the components was not permitted. Thus these earlier patents disclosed mechanical arrangements by which one of the components could move only up and down, or could only move sideways. In FIG. 4C this desired result is achieved using a pantographic mechanism 220 as constraint mechanism 215 Pantographic mechanism 220 permits movement of film 290, attached to the internal distal end of arm 190, relative to a fixed second film 300, without permitting relative rotation between the two films. As such, film 290 (with its grid-like pattern) can move in any direction relative to film 300 (with its grid-like pattern), except for relative rotational movement. In FIG. 4C, film 290 is intentionally drawn somewhat to the right of film 300, for ease of understanding the relationship between the two films. Those skilled in the art will appreciate that optical gain in detecting relative movement with a pantographic mechanism such as 220 can be obtained by using differently sized components in implementing the mechanism.

The evolution of pantographic mechanism 220 in FIG. 4C follows from the simpler mechanisms shown in FIGS. 4A and 4B. In FIG. 4A, spaced apart arms 310 are secured by pivot mechanism 330 at lower ends to a base member 340 and at upper ends to an upper member 350. It will be appreciated that arms 310 can be pivoted left or right, right movement shown in FIG. 4A in phantom, with the result that while upper member 350 can move, its movement is always parallel to base member 340, and never rotational.

In pantographic mechanism 220 shown in FIG. 4B, a descending portion 360 of upper member 350 is pivotally attached to the left ends of spaced apart members 370 that are pivotally joined at the opposite end to a member 380. Member 380 can be moved up and down but will always move perpendicularly to base member 340. Member 380 can also be moved left and right, but such movement will always be parallel to base member 340. Stated differently, constraint mechanism 215 in FIG. 4B comprises pantographic mechanism 220 that permits member 380 to move in two mutually orthogonal directions, but precludes rotational movement relative to base member 340.

FIG. 4C is a slight evolution of mechanism 215 and the configuration of FIG. 4B, where member 380 is now somewhat "T" shaped and functions in part as arm 190, to whose distal end is attached single control element 110. As a user moves element 110 parallel to the x-axis and/or y-axis, there results a user-controlled movement of film 290 relative to film 300 in two dimensions (e.g., parallel to the x-axis and/or y-axis, while precluding rotational movement of film 290 relative to film 300.

The pantographic mechanism 220 implementation of constraint mechanism 215 shown in FIG. 4C can be implemented using inexpensive, low mass, plastic components with an overall form factor that is smaller than the mechanical configurations shown in the '921 patent or the '991 patent. The associated electronics for processing light signals passed through the parallel films 290, 300 are known in the art, including for example electronic sensing as described in the '991 patent. As described earlier herein, switches 240, 250, and/or light emitters-detectors 230 are preferably included to detect user-intended mouse-clicks.

Figure 5A:
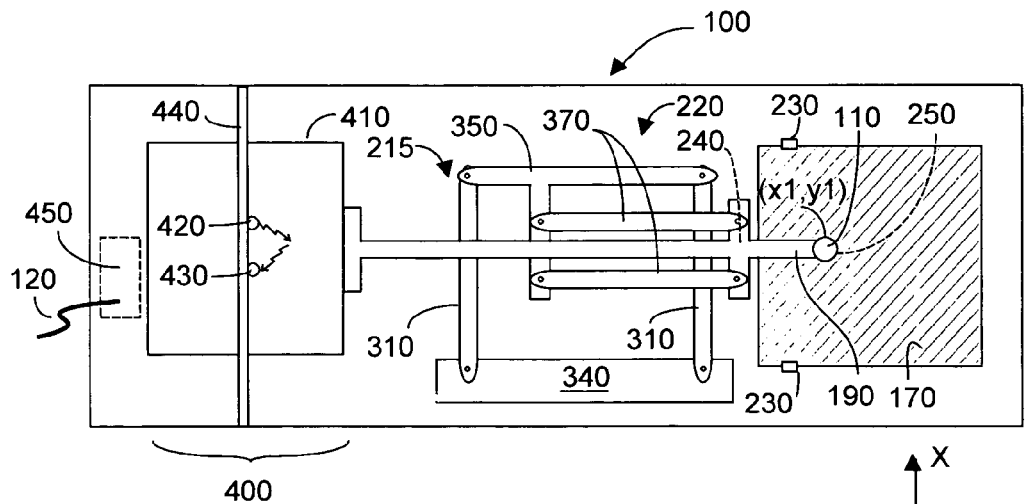
FIGS. 5A and 5B depict plan views of an exemplary optical sensing pantographically implemented embodiment of the present invention.
Figure 5B:
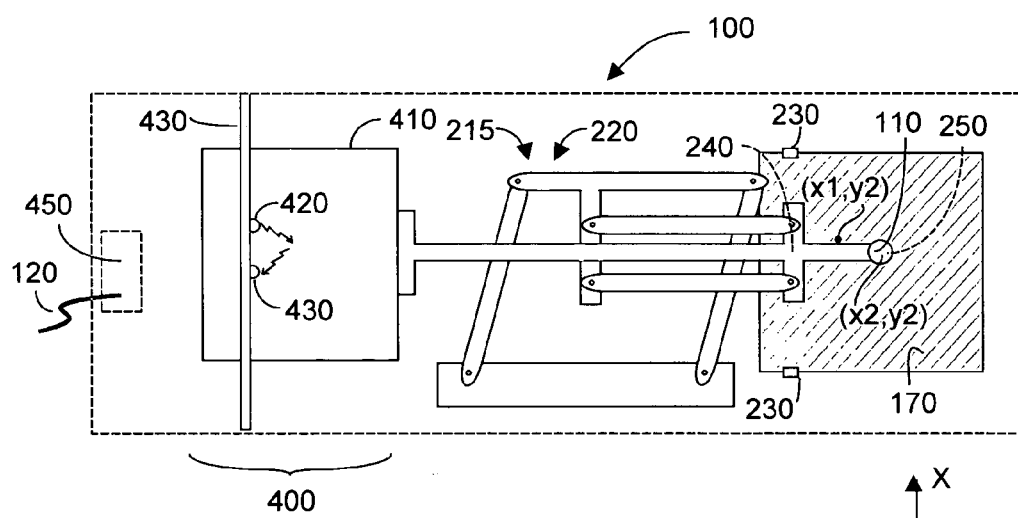

FIGS. 5A and 5B depict an embodiment of device 100 in which constraint mechanism 215 includes a pantographic or equivalent mechanism 220 that is used with an optical sensing system 400 to detect user-controlled movement of single control element 110, preferably upon surface 170. In this embodiment, mechanism 220 ensures that movement of optical reflecting surface 410 along mutually orthogonal (x,y) axis, responsive to user-manipulation of control element 110, and that no rotation of surface 410 occurs relative to the location of optical elements 420, 430 (described below). Optical elements 420, 430 are shown as being mounted on an immobile member 440 to indicate that these elements are fixed in position relative to user-movable surface 410. Optical sensing system 400 may be said to include at least one optical emitter 420, at least one optical detector 430, and a reflective surface 410, which moves relative to the fixed locations of elements 420, 430. System 400 preferably also includes associated electronics 450, which discerns from reflected optical energy detection signals the movement of surface 410 proportional to movement of control element 110.

In FIGS. 5A and 5B, as the single control element 110 is manipulated by a user across or on surface 170, proportional movement of film 410 occurs relative to a fixed position optical emitter 420 and optical detector 430. Element 420 emits optical energy towards surface 410, and at least some of the energy is reflected by surface 410 to be sensed by optical detector 430. Optical emitter(s) and detector(s) 420, 420 are coupled to electronics 450, which electronics can discern different locations on surface 410 from each other as the reflective surface is, at microscopic levels, imperfect. Surface 410 may be a plane of plastic or any other preferably lightweight and inexpensive material whose reflective surface is relatively imperfect. (The topology of surfaces such as polished glass is too uniform for use as surface 410, but most other material surfaces will work.) The functioning of optical system 400, e.g., elements 420, 430, surface 410, and electronics 450, may be as described by Gordon in U.S. Pat. No. 6,281,882 (2001) and U.S. Pat. No. 6,433,780 (2002). In brief, as single control element 110 is manipulated by the user, pantographic mechanism 200 produces responsive movement of surface 410, which movement is detected by optical elements 420, 430, which are stationary.

Comparing FIGS. 5A and 5B, the control element has been manipulated to the right and slightly downward, from point (x1,y1) to point (x2,y2). As a result light emitted by emitter(s) 420 will now reflect from a different region of surface 410. The fact that surface 410 has been moved and the direction and magnitude of the movement can be detected by detector(s) 430 and electronics 450 based upon the difference in "topology" of surface 410 resulting from the (x1,y1) to (x2,y2) movement on surface 170. Electronics 450 via cable 120 (or via infra red or wireless, which may be included as part of electronics 450) communicates the movement to the associated computer system. Display 140 (see FIG. 6) would show the movement representing (x1,y1) to (x2,y2) as a cursor locus moving left to right and slightly downward. It will be appreciated that the above-described operation is somewhat analogous to an inverted optical mouse.

It is noted that in a Gordon-type optical mouse, optical emitter(s) and detector(s) within a somewhat cumbersome mouse housing are user-moved over a typically heavy and stationary reflective surface, e.g., a desktop. By contrast, in embodiments of the present invention, a preferably very lightweight reflective surface (410) is moved relative to fixed optical emitter(s) and detector(s) (420, 430) in response to user-movement of a light weight, easily manipulated control element (110). Further, in a Gordon-type optical mouse, fingers are used for left and right mouse clicks, whereas in embodiments of the present invention, vertical movement of the single control element is used for left and right mouse clicks. In addition, a Gordon-type optical mouse does not provide absolute coordinate information to the user, whereas such information is provide in the present invention by the relative position of the control element on surface 170.

Figure 5C:
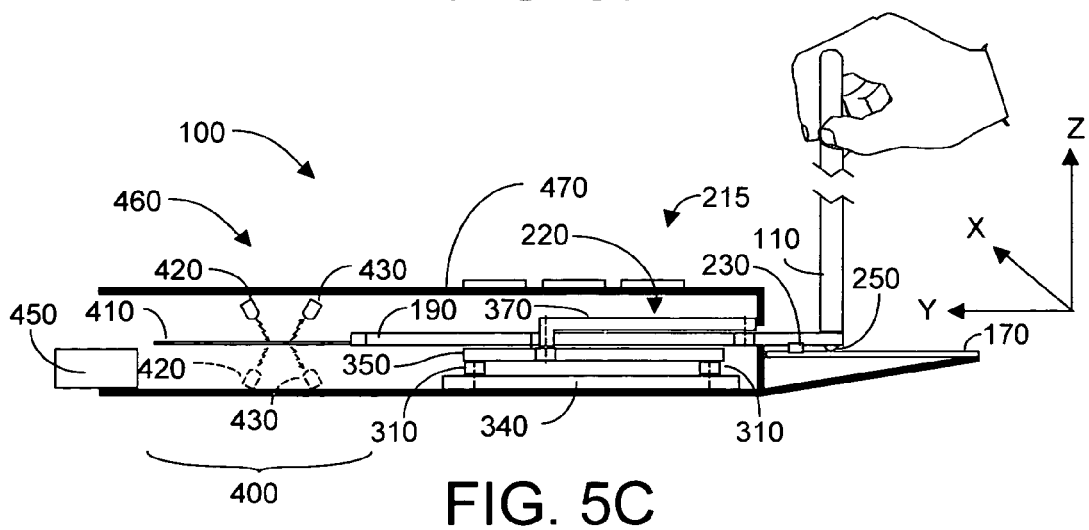
FIG. 5C is a side view of the optical sensing pantographically implemented embodiment of FIG. 5A, according to the present invention.

FIG. 5C is a cutaway side view of a keyboard 460 within whose housing 470 is disposed a pointing device 100, preferably in which constraint mechanism 215 includes a pantographic optical sensing embodiment as exemplified in FIGS. 5A-5B. As noted the form factor of pantographic mechanisms such as mechanism 220 permits fabricating pointing device 100 within a very shallow housing, for example, within housing 470 of a conventional keyboard. In the configuration shown in FIG. 5C, surface 170 protrudes from the right edge of the keyboard, although the overall dimensions of the keyboard could be increased such that surface 170 is flush with the upper surface of housing 470. Note in FIG. 5C that optical elements 420, 430 may be disposed above or below surface 410. While control element 110 is shown as being pencil-like in shape, it could instead be any other configuration suitable to the dexterity and ability of the user.

In some of the above described embodiments mechanical movement of control element 110 on surface 170 is detected, using resistive or more preferably optical techniques. However such user-controlled movement of element 110 could instead be detected using other mechanisms, preferably disposed beneath surface 170. Such other mechanisms could include without limitation, a pad that outputs resistance change responsive to force from control element 110, a pad that outputs capacitance changes responsive to force from control element 110, a pad responsive to pressure from control element 270, etc. If desired control element 110 could be metallic such that electrical charge from a user's body is conducted via control element 110 into a pad, disposed beneath the lower face of surface 170, which pad outputs a signal proportional to such electrical charge. If desired, surface 170 or a pad disposed beneath the lower face of a at least partially transparent surface 170, could respond to light emitted from an LED disposed adjacent to switch 250. As such, surface 170 or the pad would emit a signal responsive to location of control element 110 on surface 170. In general, however, the pantographic optical sensing embodiment of FIGS. 5A-5C and FIG. 6 are preferred.

Figure 7A:
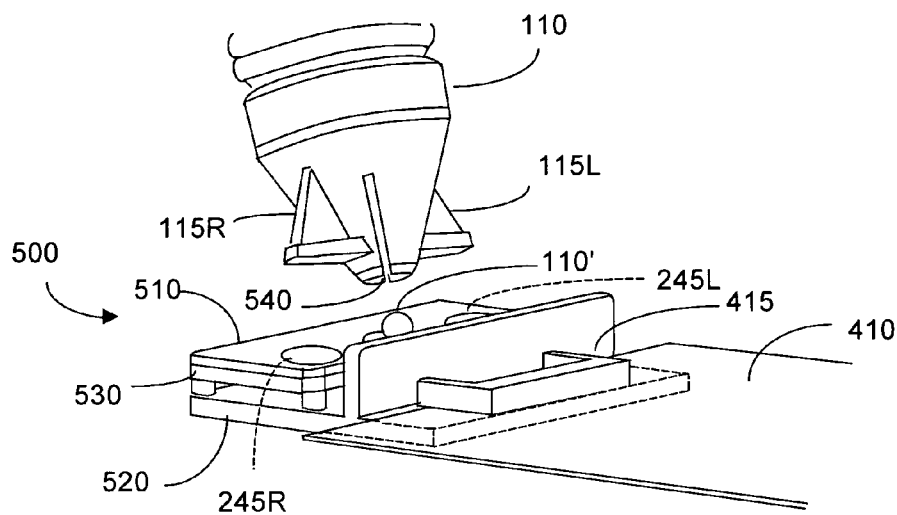
FIG. 7A is a perspective view showing modular attachment of a control element and attachment of optically reflective material to a control element moved platform, according to an embodiment of the present invention.

FIG. 6A is a perspective view of an embodiment of the present invention in which constraint mechanism 215 is implemented with mating slots and vanes rather than pantographically. In FIG. 6A user manipulation of a single control element 110 moves an optical reflecting surface 410 along mutually orthogonal (x,y) axis in response to the manipulation. Housing 200 of device 100 preferably includes left and right upwardly projecting vanes 105L and 105R disposed parallel to the y-axis, as shown. A platform 500 is user-moveable with respect to housing 200 in the (x-y) plane, for example by manipulating a single control element 110. Element 100 is preferably modularly attachable to platform 500, for example by snapping onto a sphere 110', best seen in FIG. 7A. As seen in FIG. 8C, platform 500 is constrained to move parallel to the (x-y) axes by the interaction of slot 620 formed parallel to the x-axis in a member 600 that is constrained to slide parallel to the y-axis by the interaction of vanes 105L, 105R and slots such as 610 (only one of which is shown) formed parallel to the y-axis. These vanes and slots mate slidingly such that a relatively frictionless slide results, the motion being constrained to be parallel to one of the two orthogonal axes. Optical reflecting surface 410 is attached to platform 500, for example by a retainer 415. Thus, as a user moves control element 110, platform 500 and optical reflecting surface 410 are moved parallel to the (x,y) axes, but are constrained from any rotational movement.

Optical elements 420, 430 are fixedly attached within housing 200, and may be as described with respect to FIGS. 5A and 5B, and may be located above or below surface 410. User movement of control element 110 moves optical reflecting surface 410 such that the movement is constrained to be parallel to the (x,y) axes without permitting rotation of surface 410 relative to the location of optical elements 420, 430. As in the earlier-described optical embodiments, device 100 in FIG. 6A includes associated electronics 450, which discerns from reflected optical energy detection signals the movement of surface 410 proportional to movement of control element 110. While device 100 is shown as being connectable via a cable 120 to a companion device (perhaps computer system 140 in FIG. 9), it is understood that electronics 450 could if desired also output appropriate signals to a companion device wirelessly, for example using Bluetooth technology.

It will be appreciated that the embodiment of FIG. 6A advantageously requires that the user manipulate only the mass of surface 410 and platform 500, which is connected to surface 410 by retainer 415. Preferably housing 100 including platform 500 and retainer 415 are made from lightweight inexpensive material, for example injection molded plastic. As such, platform 500 and retainer 415 advantageously present very little mass for the user of device 100 to move, to affect cursor movement. In contrast to prior art optical mice, the present invention maintains the optical sensors stationary and moves surface 410 relative to these sensors.

Experiments by applicant show that the amount of force required to move surface 410, frame 415, and platform 500 (to which element 110 preferably is modularly attachable) is about 4% of the force required to move a conventional optical mouse. The ability to manipulate device 100 using only 4% of the force required to manipulate a prior art mouse can substantially reduce the amount of stress on the user's hand (or foot or other body part). This substantial reduction in required force can substantially reduce user fatigue and susceptibility to repetitive stress syndrome (RSI).

Various modes of mouse clicking for the embodiments of FIGS. 6A-8C will now be described. In overview, the present invention can reduce the repetitive aspect of RSI by allowing the user to alter the manner by which mouse clicks are implemented. In the embodiments of FIGS. 6A-8C, left or right mouse clicking is sensed and enabled using a touch sensor switch 245L or 245R, mounted in platform 500. A third touch sensor switch 245C preferably is also mounted in platform 500, directly below the attachment of single control element 110 to the platform. Sensor switches 245L, 245C, 245R may be implemented in a variety of ways, including without limitation use of mechanical microswitches, capacitive sense switches, and so forth.

Figure 7B:
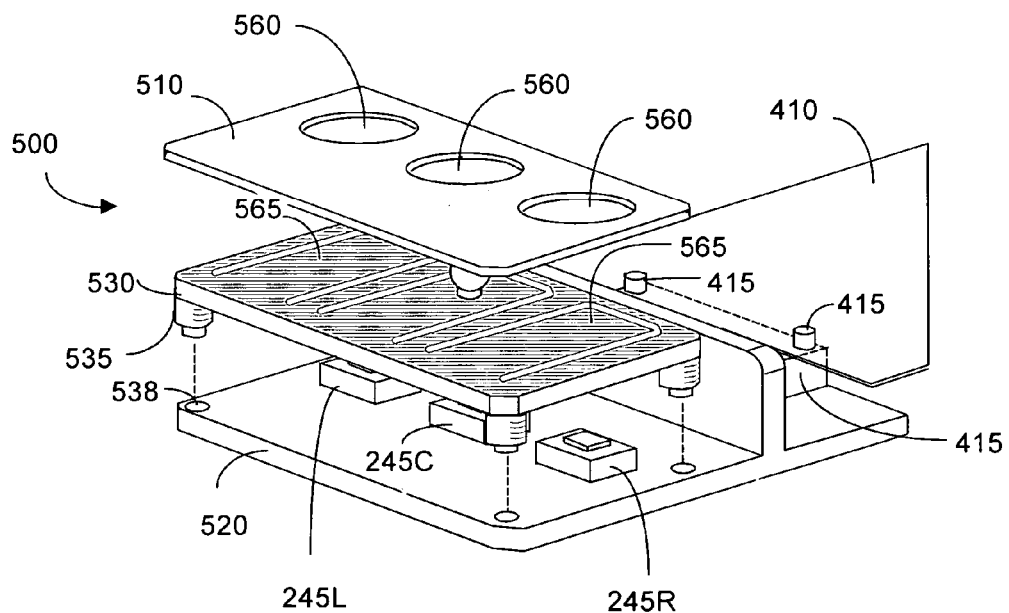
FIG. 7B is a perspective break-away view showing a control element moved platform, according to an embodiment of the present invention.

As best seen in FIG. 7B, platform 500 preferably comprises an upper platform member 510 preferably made of rubber having a through-opening 560 formed above each touch sensor switch to facilitate switch access. Platform 500 further comprises an intermediate platform member 530 that defines a user-deflectable cantilever section 565 generally beneath through-openings 560 and above the associated touch sensor switch. Platform 500 further comprises a lower platform 520 that is shown attached to intermediate platform 540 using corner located intermediate platform member 520 downwardly facing projections 535 that mate with openings 538 in the upper surface corners of lower platform 520. Platform 500 can of course be implemented otherwise.

Figure 8A:
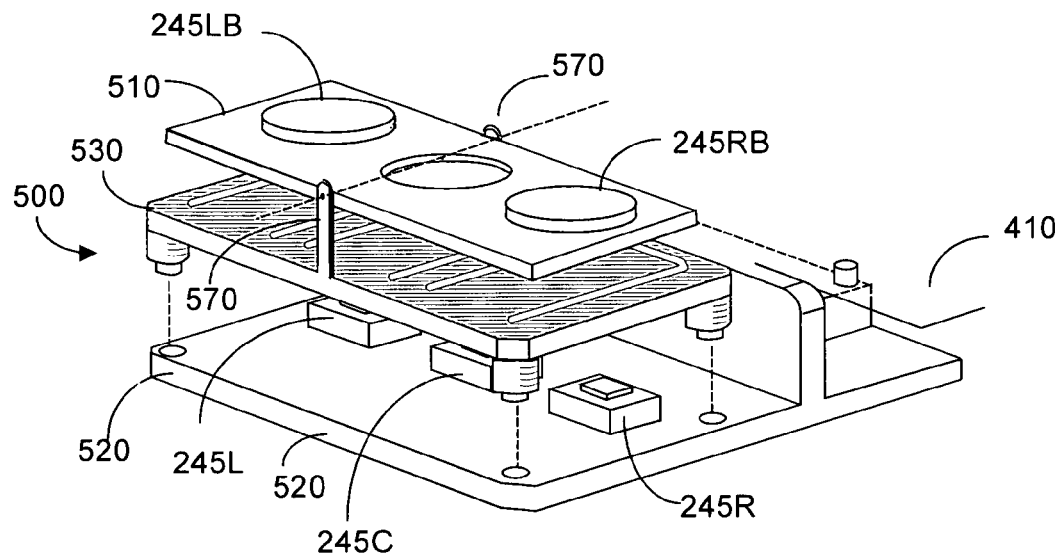
FIGS. 8A and 8B are perspective views of a tilt-platform used to emulate mouse clicks, according to an embodiment of the present invention.
Figure 8B:
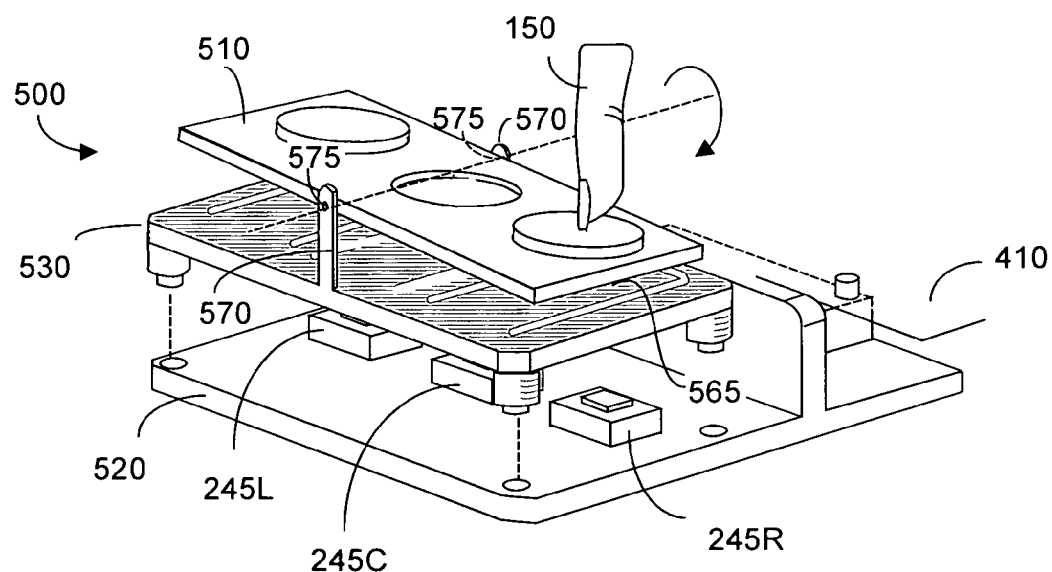
Figure 8C:
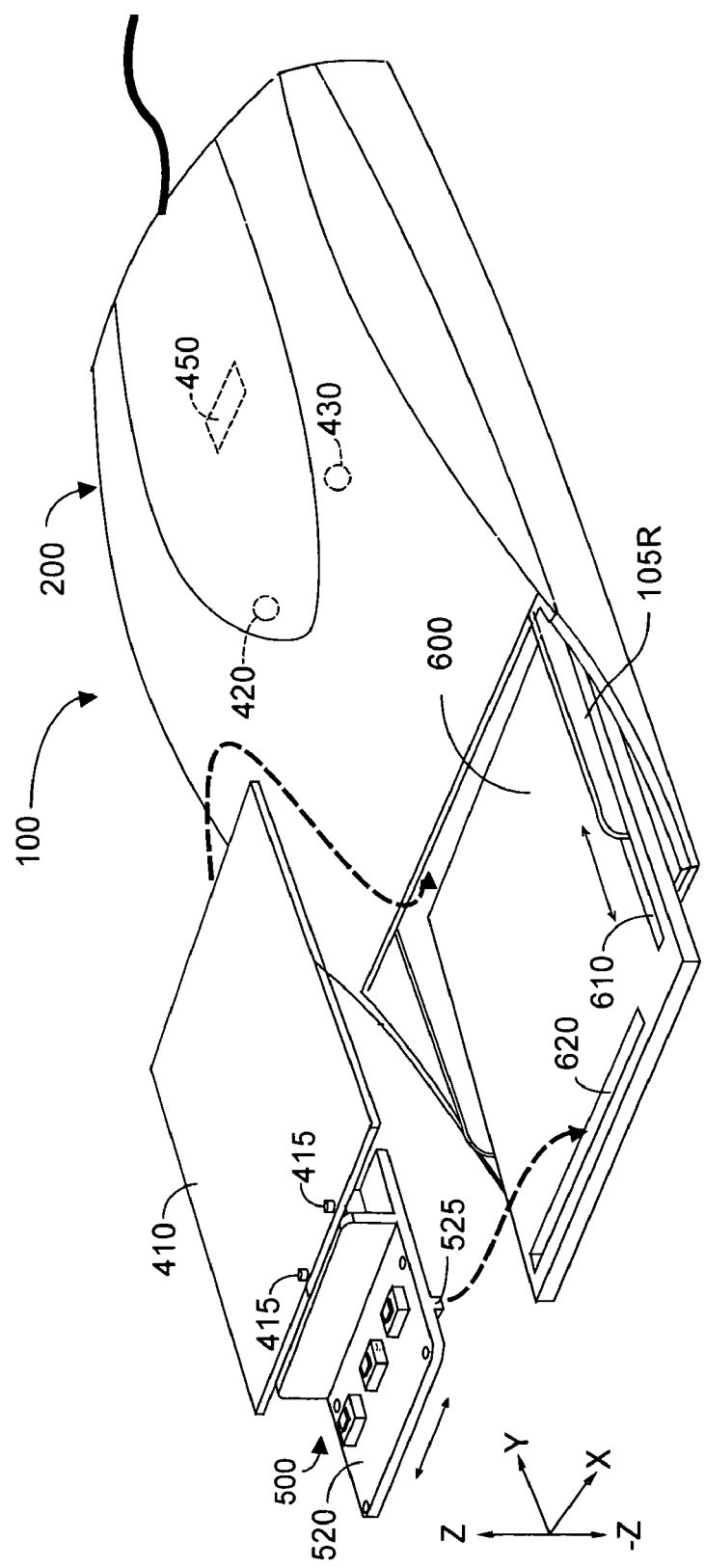
FIG. 8C is a perspective break-away view showing a mechanism to constrain (x-y) axis movement of the optically reflective material responsive to user movement of the control element, according to an embodiment of the present invention.

In the embodiments of FIG. 6A, 8A, 8B, the user can simply left or right mouse click (or double mouse click) by pressing touch sensor switch 245L or 245R once or twice rapidly, for example with a finger 150. The embodiment of 8A and 8B includes a modified platform 500 that provides a teeter-totter like function to facilitate left and right mouse clicking (including double mouse clicking). In this embodiment, intermediate platform member 530 includes two spaced-apart support arms 570. Pivot pins 575 pivotally secure the central edges of upper platform member 510 to the distal ends of support arms 570. Preferably left and right openings 560 in the upper support member are filled with left and right buttons 245LB, 245RB. With no user force applied to upper platform member 510, the plane of the upper platform member is neutral, e.g., parallel to the (x-y) plane. But the slightest force applied to either the left or right button 245LB, 245RB will cause upper platform member 510 to tilt about a rotation axis (shown by a phantom line through pivot pins 575. For example in FIG. 8B, the user's finger 150 is shown depressing right button 245RB, which causes a slight clockwise rotation of upper platform member 530. The underlying cantilevered member is deflected downward (due to the flexible nature of the preferably thin-walled upper platform member), and touch sensor switch 245R is activated, emulating a right mouse click. Had the user pressed the left button 245LB, touch sensor switch 245L would have emulated a left mouse click. Two quick presses of a button would emulate a double-mouse click. Preferably center switch 245C is mounted slightly higher than adjacent switches 245L, 245R, or is selected to require slightly less downward force for activation. As a result, the slightest downward force upon control element 110 will activate switch 245C. It is understood that switch 245C can, if desired, be dedicated to a desired mouse function, for example double-clicking, triple-clicking, etc.

Figure 6B:
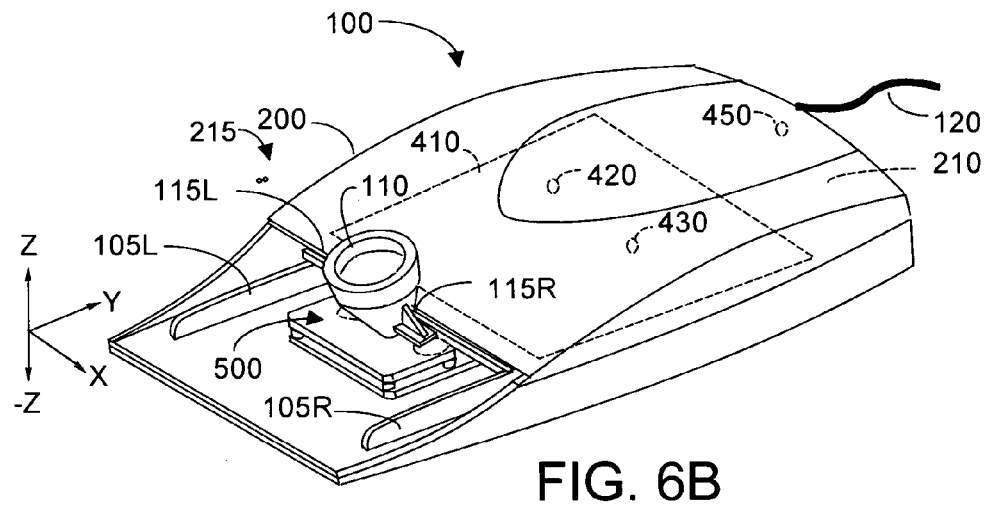
Figure 6C:
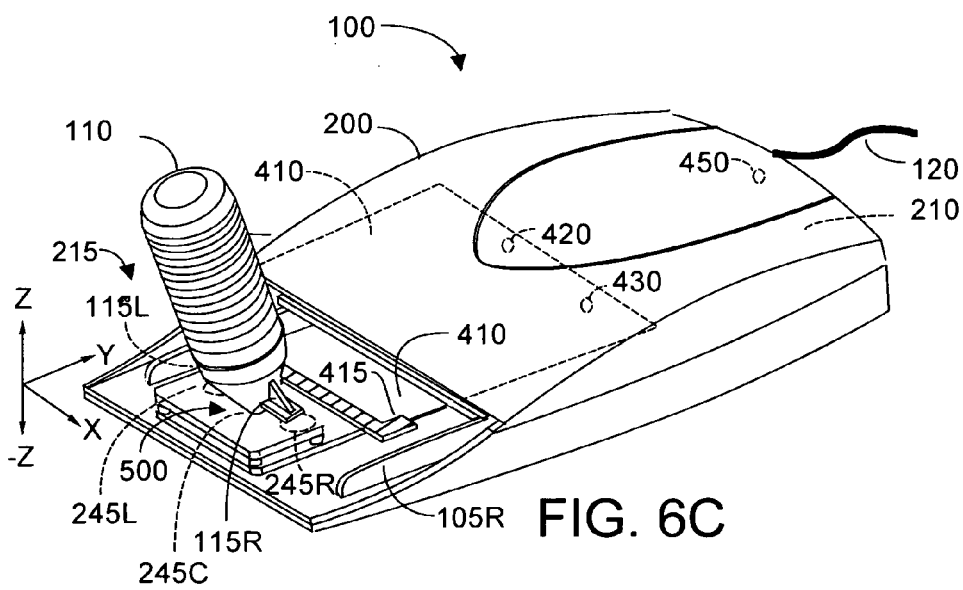

As best seen in FIG. 7A, the preferably modular attachment of single control element 110 to platform 500 can be facilitated by forming mating interconnectable sections of these components. For example an upwardly projecting sphere 550 can be formed as part of platform 500, generally over the region of sensor switch 245C, and a mating sphere-shaped concavity 540 can be formed in the lower distal region of single control element 110. The control element can thus be snapped onto sphere 550 for attachment to device 110, and can be readily pulled off sphere 550 for detachment. FIG. 6B shows a modularly attached control element 110 having an opening into which a finger or toe might be inserted to manipulate device 100. In FIG. 6C, a pencil-like stylus control element 110 has instead been modularly attached to device 110. If desired, the stylus control element can comprise an inner core that is perhaps a plastic rod terminating in the sphere-shaped concavity 540, and an outer foam cylinder that fits over the core. It will be appreciated, however, that the ability of the present invention to modularly attach and detach control elements 110 enables the user to change control elements at will. For example if the user's hand become fatigued after using a thin pencil-shaped stylus 110, the user might detach that stylus and continue working using a larger diameter stylus 110. Or, the same device 110 may be used by a handicapped person perhaps with a control element such as shown in FIG. 6B, and then used by a non-handicapped person, perhaps with a stylus such as shown in FIG. 6C.

Not only does the present invention provide user flexibility in selecting a desired control element 110, but flexibility is also provided in the manner of emulating mouse clicks. For example, in the embodiments of FIGS. 6A, 8A and 8B, the user's finger can be used to command single or double mouse clicking, without involving the control element. In the embodiments of FIGS. 1-5C, user movement of the control element 110 primarily up or down (e.g., in a direction normal to the (x-y) plane was used to command single or double mouse clicking. In the embodiments of FIGS. 6B, 6C and 7A, user-movement of single control element 110 is used to emulate mouse clicks, but by tilting the control element relative to the (x-y) plane. It is seen that in FIGS. 6B, 6C, 7A, the lower distal end of control element 110 includes left and right wing protrusions 115L, 15R. When control element 110 is attached to platform 500, these wing protrusions extend laterally so as to overlie sensor switches 245L, 245R respectively. In these embodiments, left and right mouse clicking may be enabled simply by tilting control element 110 slightly to the left or to the right, e.g., away from the vertical axis. Such tilting will cause the respective wing protrusion to interact with the underlying respective sensor switch so as to command mouse clicking. Double mouse clicking can be commanded by two rapid tilts of control element 110.

FIG. 8C depicts in detail the slot-vane implementation of constraint mechanism 215 by which movement of optical reflecting surface 410 is constrained to move parallel to the (x-y) axes, according to the present invention. In the embodiment shown, a longitudinal vane 525 extends from the lower surface of lower platform member 520 parallel to the x-axis. Vane 525 preferably extends the x-dimension width of the lower platform member. When platform 500 is movably connected to housing 200, vane 525 inserts into a first longitudinal slot 620 formed in planar member 600, preferably fabricated from light weight material, such as injection molded plastic. As such, platform 500 may readily be moved left or right along the x-axis by user manipulation of platform 500 via control element 110 (not shown in FIG. 8C). Planar member 600 also has a second longitudinal slot 610 formed near an edge of the member, parallel to the y-axis. When platform 500 is movably connected to housing 200, right housing vane 105R will project upward through second slot 610. As such, platform 500 may be readily moved in or out along the y-axis by user manipulation of the platform via control element 110 (not shown). It is understood that when platform 500 is movably attached to housing 200, optically reflective material 410 will be within the housing. As the user manipulates the control element, platform 500 moves along the (x-y) axes, and moves optically reflective material 410. As noted earlier, optically reflective material is attached to platform 500, for example using retainer(s) 415. User manipulation of the control element is sensed by the optical sensor system comprising components 420, 430, 450, and cursor position information is output by electronics 450, via wire or otherwise, to a companion device. Mouse click information is also output via electronics 450, again via wire or otherwise.

Various embodiments of the present invention have been described with respect to a constraint mechanism 215 that may be implemented pantographically, or with mating vanes and slots. In practice, applicant has found the pantographic implementation to yield somewhat superior cursor control, probably because the vane-slot implementations can sometimes exhibit friction, especially when moving the control element diagonally. Further, pantographic implementations can be inexpensively produced using very light weight plastics, although other materials could be used.

Figure 9A:
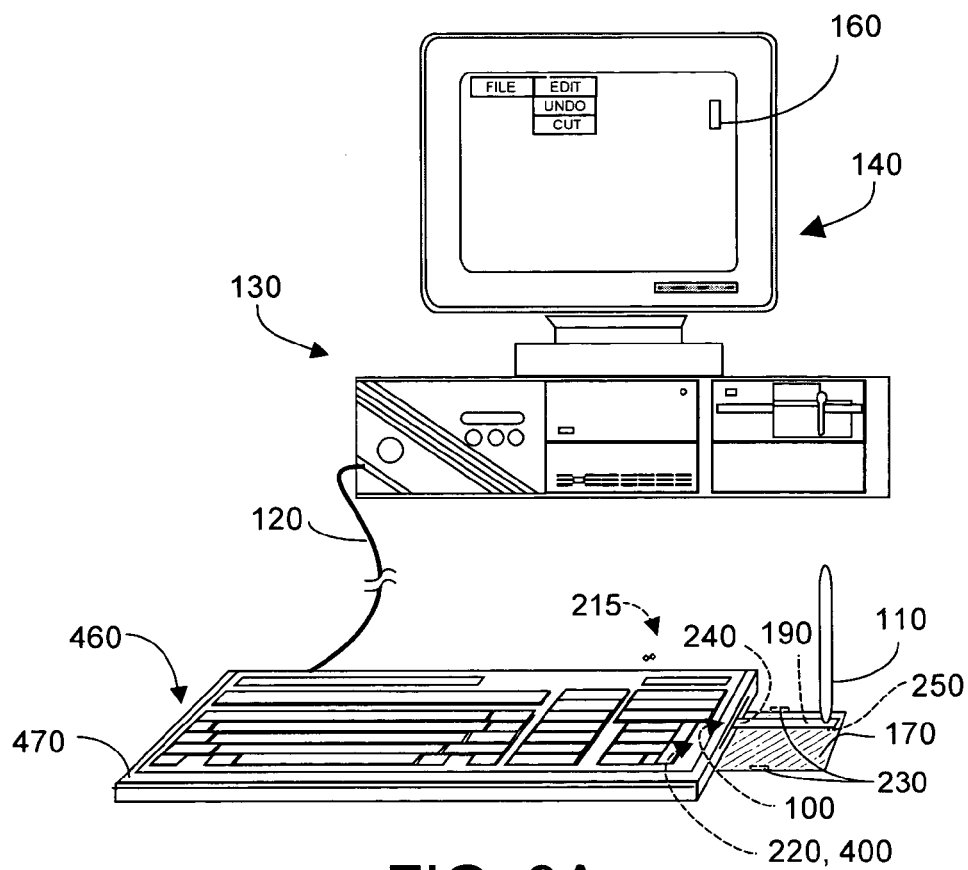
FIGS. 9A and 9B depict embodiments of the present invention disposed within a computer keyboard, a computer laptop or other computer appliance.
Figure 9B:
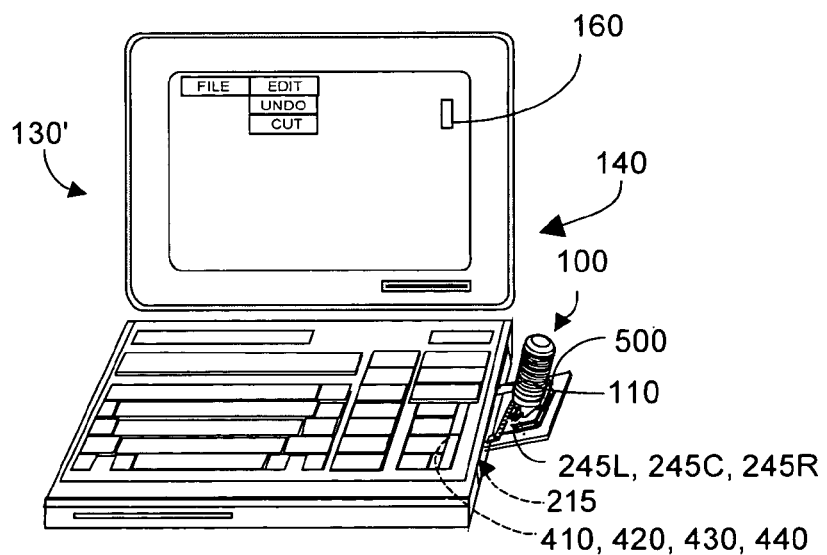

In general, the overall size of housing 200 as shown in the embodiments of FIGS. 6A-6C and 8C are approximately 4" (10 cm) in length by about 3" (7.6 cm) in width by about 1" (2.5 cm) in height, excluding the length of control element 110. The housing components preferably are made from an inexpensive, lightweight material such as injection molded plastic FIG. 9A is a perspective view of keyboard 460 with an embodiment of device 100 according to FIG. 1-5C fabricated within the keyboard housing, while FIG. 9B is a perspective view of a laptop computer 130' that has device 100 incorporated into the laptop housing, according to the embodiments of FIGS. 6A-8C. In FIG. 9B it is understood that a computer appliance other than laptop computer 130' could have device 100 incorporated into its housing.

In summary, there any many techniques useable with the present invention to provide a signal proportional to location of control element 110 on surface 170, or proportional to its general location on device 100. Regardless of the technique used, the resultant device 100 can be used to provide absolute coordinate information. Further, embodiments of the present invention using optical detection are operable using a small fraction (e.g., perhaps only about 4%) of the force required to manipulate a conventional mouse device. The ability to manipulate a cursor using only 4% of the force required by conventional devices can substantially reduce the likelihood of repetitive stress injury. Further the ability to reduce the repetitiveness of device operation by changing control elements and/or the manner in which mouse clicking is commanded can also substantially reduce the likelihood of repetitive stress injury. In addition, users can benefit from the present invention even if the user is handicapped, especially as a result of the use of a single control element.

Modifications and variations may be made to the disclosed embodiments without departing from the subject and spirit of the invention as defined by the following claims.

What is claimed is:

1. A single control element device that is operable in an absolute coordinate mode and enables user control of a computer cursor and emulation of mouse clicks, the device comprising:
    a single control element manipulable by a user of said device;
    a surface defining an x-y plane relative to which said single control element is manipulable by said user;
    means for resolving user movement of said single control element relative to said x-y plane of said surface and for outputting a computer recognizable signal therefrom; and
    means for recognizing user manipulation of said single control element in at least one of (a) an axis normal to said x-y plane and (b) an axis tilted with respect to said x-y plane, and means for discerning therefrom at least one emulated mouse click, said means for discerning including a reflective element coupled for movement along an x-axis and a y-axis of said x-y plane responsive to movement of said single control element and including an optical sensing system disposed to optically sense x-axis and y-axis movement of said single element in said x-y plane;
    wherein observation at any time of relative position of said single control element on said x-y plane of said surface provides said user with information as to relative position of a cursor on a computer display controlled by said device.

2. The device of claim 1, wherein said optical sensing system includes:
    at least one stationary light transmitter disposed to direct light upon said reflective element; and
    at least one stationary light detector disposed to detect light from said light transmitter reflected by said reflective element.

3. The device of claim 1, wherein said means for recognizing discerns at least one of a left mouse click, a double mouse click, and a right mouse click.

4. The device of claim 1, wherein said means for recognizing discerns at least two of a left mouse click, a double mouse click, and a right mouse click.

5. The device of claim 1, wherein said means for recognizing user manipulation includes at least one of (a) a sensor and (b) a sensor switch, disposed to respond to said user manipulation.

6. The device of claim 1, wherein said means for recognizing user manipulation includes at least a first sensor switch operable to command at least a left mouse click, and a second sensor switch operable to command at least a right mouse click.

7. The device of claim 6, wherein said single control element includes left and right lateral regions that overlie respectively said first sensor switch and said second sensor switch.

8. The device of claim 6, further including a platform tiltably mounted to said housing and having left and right distal regions overlying said first sensor switch and said second sensor switch.

9. The device of claim 6, wherein said first sensor switch and said second sensor switch are operable by at least one of (a) force from a user's finger, (b) vertical movement of said single control element in a plane normal to said (x-y) plane, and (c) tilting movement of said single control element in a plane not normal to said (x-y) plane.

10. The device of claim 1, wherein said single control element is modularly attachable to said device and is manipulable by at least one of (a) a single finger of said user, (b) a hand of said user, and (c) a toe of said user.

11. The device of claim 1, further including a housing that houses at least a portion of said device, said housing also housing a computer keyboard.

12. The device of claim 1, wherein said means for resolving includes a pantographic mechanism having a first member moved by said single control element and having a second member to which said reflective element is coupled.

13. The device of claim 1, wherein said surface has a dynamic coefficient of friction such that friction between said surface and said single control element increases with decreasing rate of movement of said single control element on said surface.

14. A single control element device that enables user control of a computer cursor and emulation of mouse clicks and is operable in an absolute coordinate mode, the device comprising:
    a device housing;
    a single control element, modularly attachable to a portion of said housing, manipulable by a user of said device;
    a surface defining an x-y plane relative to which said single control element is manipulable by said user;
    an optically reflective member, disposed at least partially within said housing, moveable parallel to (x-y) axes of said (x-y) plane responsive to manipulation of said single control element;
    means, disposed within said housing, for constraining movement of said single control element and movement of said optically reflective member to movement along an x-axis and a y-axis within said x-y plane;
    an optical sensor system, disposed in said housing, to detect (x-y) movement of said single control element using light reflected from said optically reflective member, said optical sensor system also outputting a computer recognizable signal therefrom; and means for emulating at least one of (a) a left mouse click, (b) a double left mouse click, (c) a right mouse click, and (d) a double right mouse click, said means for emulating disposed at least partially within said housing;

wherein observation at any time of relative position of said single control element on said x-y plane of said surface provides said user with information as to relative position of a cursor on a computer display controlled by said device.

15. The device of claim 14, wherein said means for emulating includes at least one of (a) a sensor and (b) a sensor switch responsive to user movement of said single control element in an axis normal to said x-y plane.

16. The device of claim 14, wherein said means for emulating includes at least one of (a) a sensor and (b) a sensor switch responsive to user movement of said single control element in an axis tilted with response to said x-y lane.

17. The device of claim 14, wherein said means for emulating includes at least one sensor switch responsive to force from said user.

18. The device of claim 14, wherein said single control element is modularly attachable to said device and is manipulable by at least one of (a) a single finger of said user, (b) a hand of said user, and (c) a toe of said user.

19. A method to enable user control of a computer cursor and emulation of mouse clicks using an absolute coordinate single control element, the method comprising:

providing a single control element manipulable by a user relative to an x-y plane to move said cursor and in an axis selected from a group consisting of (i) normal relative to said x-y plane to emulate mouse clicks, and (ii) tilted relative to said x-y plane to emulating mouse clicks;

mechanically coupling an optically reflective element to said single control element such that user manipulation of said single control element moves said optically reflective element parallel to (x-y) axes of said plane;

optically sensing light reflected by movement of said optically reflective element so as to output a computer recognizable signal responsive to detected said movements; and generating left and right mouse clicks responsive to user movement of said single control element in at least one manner selected from a group consisting of (a) vertical movement relative to said x-y plane, and (b) tilting movement relative to said x-y plane;

wherein observation at any time of relative position of said single control element on said x-y plane of said surface provides said user with information as to relative position of a cursor on a computer display controlled by said device.

* * * * *